US007795405B2

(12) United States Patent
DiNovo

(10) Patent No.: US 7,795,405 B2
(45) Date of Patent: Sep. 14, 2010

(54) PROCEDURE FOR THE FRACTIONATION OF PROTEINS BY USING SEQUENTIAL ION EXCHANGE AND HYDROPHOBIC INTERACTION CHROMATOGRAPHY AS PREFRACTIONATION STEPS BEFORE ANALYSIS BY TWO DIMENSIONAL ELECTROPHORESIS

(75) Inventor: Augustine DiNovo, Charleston, SC (US)

(73) Assignee: Guild Associates, Inc., Dublin, OH (US)

(*) Notice: Subject to any disclaimer, the term of this patent is extended or adjusted under 35 U.S.C. 154(b) by 0 days.

(21) Appl. No.: 11/668,319

(22) Filed: Jan. 29, 2007

(65) Prior Publication Data
US 2007/0181427 A1 Aug. 9, 2007

Related U.S. Application Data

(63) Continuation-in-part of application No. 11/199,601, filed on Aug. 9, 2005, now abandoned.

(60) Provisional application No. 60/599,957, filed on Aug. 9, 2004.

(51) Int. Cl.
C07K 1/26 (2006.01)
C07K 1/28 (2006.01)
C07K 1/18 (2006.01)
C07K 1/20 (2006.01)

(52) U.S. Cl. ............. 530/412; 530/344; 530/416; 530/417

(58) Field of Classification Search ............. 530/412, 530/344, 416, 417
See application file for complete search history.

(56) References Cited

U.S. PATENT DOCUMENTS 4,894,439 A 1/1990 Dorin et al.
5,468,847 A 11/1995 Heilmann et al.

FOREIGN PATENT DOCUMENTS

JP 2003 149204 A 5/1921

OTHER PUBLICATIONS

Krapfenbauer et al., "Changes in the level of low-abundance brain proteins induced by kainic acid," Eur J Biochem 268:3532-3537, 2001.*
Lescuyer et al., "Comprehensive proteome analysis by chromatographic protein prefractionation," 25(7-8):1125-1135, Apr. 2004.*
General Electric, instructional brochure for Re RESOURCE® Q and RESOURCE® S columns, 2002.*

(Continued)

Primary Examiner—Karen Cochrane Carlson
Assistant Examiner—Rosanne Kosson
(74) Attorney, Agent, or Firm—Baker Botts L.L.P.

(57) ABSTRACT

After the sequencing of the human genome, great interest has developed in trying to discern the complementary proteome of humans and other species. The present disclosure provides devices, systems, and methods for proteomic fractionation that may increase the number of protein spots visualized by 2DE analysis, and may allow enrichment of proteins normally not detectable by standard 2DE analysis. According to some embodiments of the disclosure, devices, systems, and methods of the disclosure relate to fractionating a proteome on the basis of surface charge, hydrophobicity, isoelectric point and/or size.

19 Claims, 2 Drawing Sheets

OTHER PUBLICATIONS

International Search Report and Written Opinion for International Patent Application No. PCT/US2005/028237 (12 pages), Feb. 2, 2006.

Righetti, P.G.; "Prefractionation Techniques in Proteome Analysis"; Proteomics, vol. 3 (pp. 1397-1407), 2003.

Butt, A.; "Chromatographic Seperations as a Prelude to Two-Dimensional Electrophoresis in Proteomics Analysis"; Proteomics, vol. 3 (pp. 42-53), 2003.

Fortis, F. et al.; "Amphoteric, Buffering Chromatographic Beads for Proteome Prefractionation. I: Theoretical Model"; Proteomics, vol. 5 (pp. 620/628), 2005.

http://www.biocompare.com/prorev.asp?profrevid=101 ; "BioRad's Rotofor Cell System"; www.biocompare.com (3 pages), Mar. 1, 2006.

http://www.designawards.com.au/ADA/02-03/INDUSTRIAL%20DESIGN/026/026.HTM ; "026-02-03 : Gradiflow BF400"; Industrial Design; www.designawards.com (5 pages), Mar. 1, 2006.

Westermeier et al., "Proteomics in Practice: A Laboratory Manual of Proteome Analysis", 2002, Chapter 2, Wiley-VCH Verlag GMBH, 2002.

Fountoulakis et al., "Enrichment of Low-Copy-Number Gene Products by Hydrophobic Interaction Chromatography", Journal of Chromatography A, 1999, 833, pp. 157-168, 1999.

* cited by examiner

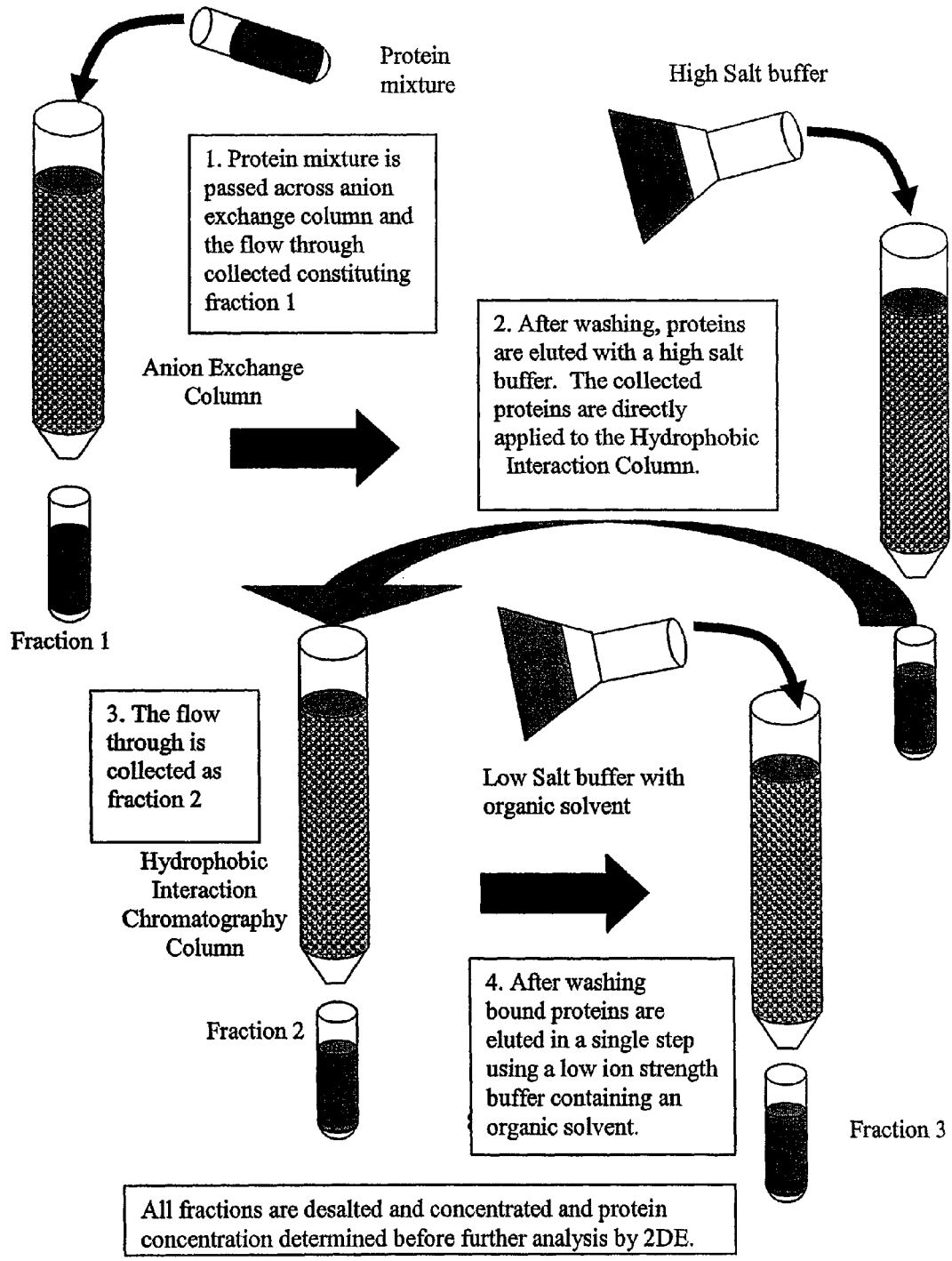
Figure 1 Basic Sequential Prefractionation Scheme Using a Three Fraction Strategy.

Figure 2: 2DE analysis of HT-29 human carcinoma cell line cytosol comparing no prefractionation (A) and after a two sequential column binary prefractionation (B-D). Iso-electric focusing pH range is 3-10, and SDS-PAGE dimension utilizes a 12% acrylamide concentration

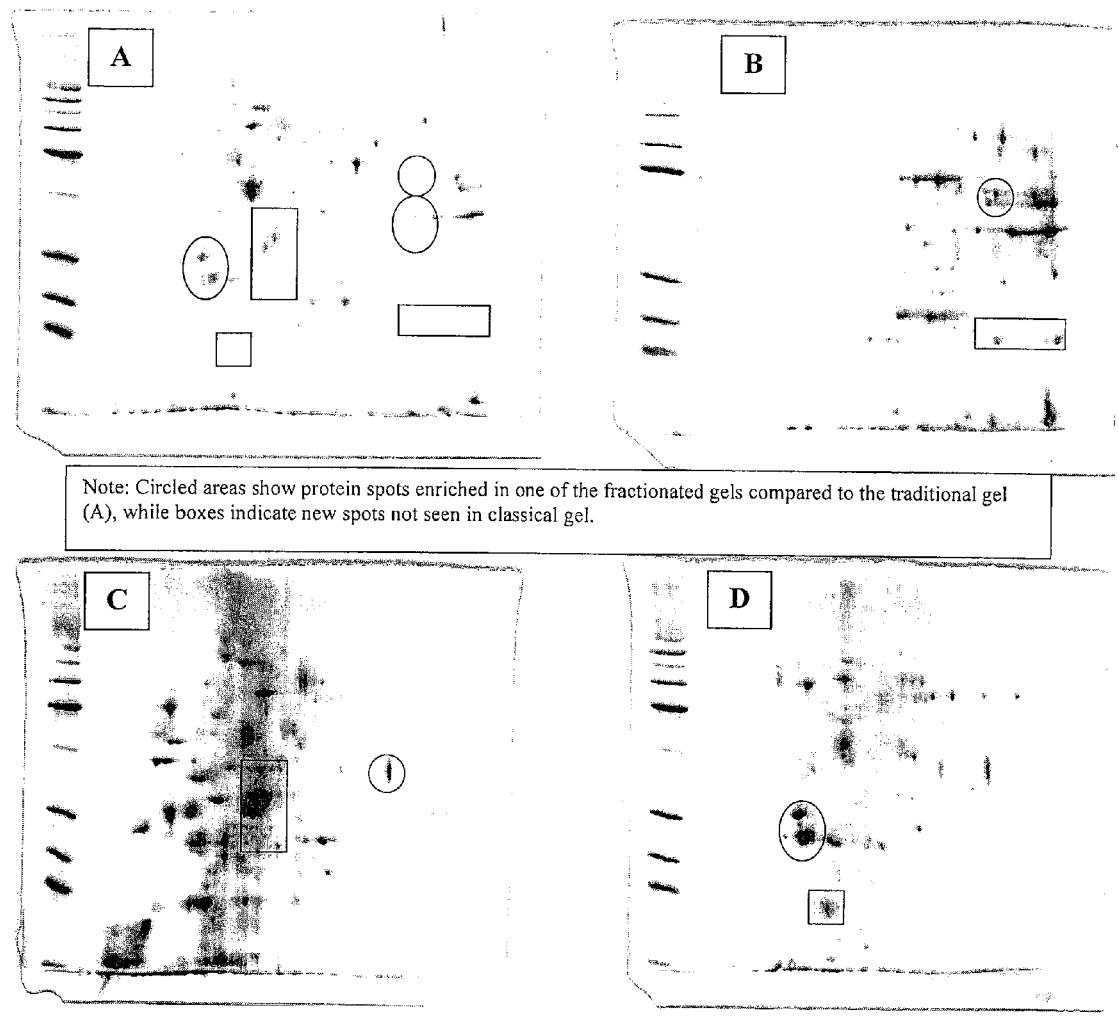

Note: Circled areas show protein spots enriched in one of the fractionated gels compared to the traditional gel (A), while boxes indicate new spots not seen in classical gel.

PROCEDURE FOR THE FRACTIONATION OF PROTEINS BY USING SEQUENTIAL ION EXCHANGE AND HYDROPHOBIC INTERACTION CHROMATOGRAPHY AS PREFRACTIONATION STEPS BEFORE ANALYSIS BY TWO DIMENSIONAL ELECTROPHORESIS

RELATED APPLICATION

This application is a continuation-in-part of U.S. patent application Ser. No. 11/199,601, filed on Aug. 9, 2005, now abandoned, which also claims priority to U.S. Provisional Patent Application Ser. No. 60/599,957, filed Aug. 9, 2004, the contents of which are hereby incorporated in their entirety by reference.

TECHNICAL FIELD OF THE DISCLOSURE

The present disclosure relates to devices, systems, and methods for fractionating proteins.

BACKGROUND OF THE DISCLOSURE

A number of approaches have been used to try to increase the number of proteins identified by 2DE analysis. Some researchers have prefractionated starting material into organelle specific fractions. This can be either a simple two-part fractionation such as membrane bound and non-membrane bound proteins, or more complicated separations using ultra centrifugation to separate out specific organelles. These methods require expensive equipment (an ultra centrifuge), and only enrich proteins of a given organelle rather than truly improving resolution. These methods may be useful in specifically investigating the expression patterns of a given organelle or compartment, but may be too cumbersome to be applied in looking at all of the proteins in the proteome.

According to another prefractionation methodology, differential solubility may be used to separate proteins into fractions. Raw material may be sequentially processed in buffers with progressively stronger detergents, and chaotropic agents, to separate proteins based upon their hydrophobic/hydrophilic characteristics. Unfortunately, such methods result in a lot of proteins being present in more than one fraction which increases the difficulty of analysis. Other methods use other electrophoretic techniques such as preparative isoelectric focusing or preparative electrophoresis to prefractionate raw material into discrete fractions. These also require special relatively expensive equipment, and may be time consuming. Use of a liquid phase isoelectric focusing apparatus has been the most vigorously pursued of the electrophoretic approaches. Devices in commercial production such as Gradiflow (Gradipore-Frenchs Forest, NSW, Australia) or Rotofor Cell (Biorad) have been applied to this field but require fairly large volumes, and have difficulties with identifying proteins with isoelectric points near their pI cut offs.

SUMMARY OF THE DISCLOSURE

Accordingly, a need has arisen for improved methods of global protein fractionation in which each protein is present in fewer fractions ("fractions per protein" (FPP)). A non-limiting example of such a method is one that separates each protein into a single fraction, band, or spot. A need has also arisen for global protein fractionation methods that yield fractions that contain fewer protein species ("proteins per fraction" (PPF)). A non-limiting example of such a method is one in which each fraction, band, or spot contains a single protein.

In some embodiments, the present disclosure provides devices, systems, and/or methods for performing dual chromatography as a prefractionation procedure, e.g., for proteomic analysis of global protein expression using two dimensional electrophoresis. Protein fractions produced according to some embodiments of the disclosure may have a low incidence of the same proteins occurring in different fractions. This incidence may be lower than generally observed in other prefractionation approaches that operate on its scale. In some embodiments, methods of the disclosure use a "bind/no bind" load and elution scheme to create fractions, simplifying the chromatography.

The present disclosure provides methods of protein fractionation. Advantageously, the methods comprise prefractionation steps that greatly improve resolution of proteins. The methods of the disclosure may be particularly useful in proteomics applications.

In some embodiments of the disclosure, a method of protein fractionation comprises prefractionation by anionic exchange chromatography, hydrophobic interaction chromatography, and combinations thereof. A non-limiting example of a proteomic protein fractionation method of the disclosure comprises (a) applying a protein mixture to an anion exchange column, (b) eluting the anion exchange column with a high salt buffer, (c) applying the eluate to a hydrophobic interaction chromatography column, (d) eluting the hydrophobic interaction chromatography column with a low salt buffer, (e) (optional) eluting the hydrophobic interaction chromatography column with a low salt buffer comprising an organic solvent, and (f) fractionating the hydrophobic interaction chromatography column eluate (low salt eluate, low salt plus solvent eluate, and/or a combined low salt/low salt plus solvent eluate) by isoelectric focusing and polyacrylamide electrophoresis.

Embodiments of the present disclosure may provide separation of protein mixtures into a small number of fractions with defined characteristics that show only limited overlap between fractions compared to other methods. Devices, systems, and methods of the disclosure may be partially or completely automated for simple processing. According to some embodiments, low abundance proteins may be concentrated, e.g., basic proteins, and allow them to be visualized in 2DE analysis where they wouldn't be visualized using normal 2DE. See FIG. 2. In some embodiments, a device, system, and/or method of the disclosure may utilize protein surface hydrophobicity as a separation axis to gather physiochemical information. The amount of physiochemical information gathered may be more than obtained by other methods that prefractionate by size or charge only. The methodology may require only basic largely disposable bench top chromatography supplies to perform, and is therefore a low cost means of increasing the sensitivity of 2DE analysis.

A method of proteomic protein fractionation, according to some embodiments of the disclosure, may include prefractionating a protein mixture using one or more binary chromatographic modes to form one or more chromatographic eluates and fractionating one or more of the chromatographic eluates by isoelectric focusing and polyacrylamide electrophoresis. For example, prefractionating a protein mixture may include two binary chromatographic modes. A first binary chromatographic mode may include applying a protein mixture to an anion exchange column and eluting the anion exchange column with a high salt buffer (e.g., more than about 0.5 M) to form an anion exchange eluate. A second binary chromatographic mode may include applying the anion exchange eluate to a hydrophobic interaction chromatography column (e.g., under conditions wherein a hydrophilic fraction is formed) and eluting the hydrophobic interaction chromatography column with a low salt buffer (e.g., less than about 0.1 M salt) to form a low salt eluate. Fractionating one or more of the chromatographic eluates by isoelectric focusing and polyacrylamide electrophoresis may include the low salt eluate by isoelectric focusing and polyacrylamide electrophoresis. In some embodiments, a method of proteomic protein fractionation may further include eluting the hydrophobic interaction chromatography column with a low salt buffer comprising an organic solvent (e.g., 30% (v/v) methanol) to form a low salt plus solvent eluate, and fractionating the low salt plus solvent eluate by isoelectric focusing and polyacrylamide electrophoresis. A hydrophobic interaction chromatography column may include a C4 (t-butyl) functional group immobilized on a hydrophobic support. Isoelectric focusing may be performed using a pH range of from about 3 to about 10. Polyacrylamide electrophoresis may be performed on a gel comprising from about 10% to about 12% by weight polyacrylamide. A protein mixture may include, for example, from about 2 to about 100,000 different proteins. A protein mixture may include substantially every protein in an organism's proteome. Microbe, invertebrate, and vertebrate (e.g., human and non-human animal) proteomes may be of interest. A method of proteomic protein fractionation, according to some embodiments, may include applying a protein mixture to an anion exchange column to form a high pI fraction. A high pI fraction may be fractionated by isoelectric focusing and polyacrylamide electrophoresis. In some embodiments a high salt eluate, a low salt eluate, and/or a hydrophilic fraction may be desalted. A method of proteomic fractionation may include fractionating a hydrophilic fraction by isoelectric focusing and polyacrylamide electrophoresis.

A method of proteomic protein fractionation may consist of (a) applying a protein mixture to an anion exchange column under conditions wherein a high pI fraction is formed, (b) eluting the anion exchange column with a high salt buffer to form an anion exchange eluate, (c) applying the anion exchange eluate to a hydrophobic interaction chromatography column under conditions wherein a hydrophilic fraction is formed, (d) eluting the hydrophobic interaction chromatography column with a low salt buffer to form a low salt eluate, (e) fractionating the high pI fraction by isoelectric focusing and polyacrylamide electrophoresis, (f) fractionating the hydrophilic fraction by isoelectric focusing and polyacrylamide electrophoresis, and (g) fractionating the low salt eluate by isoelectric focusing and polyacrylamide electrophoresis.

A method of proteomic protein fractionation may include (a) applying a protein mixture comprising up to every protein in an organism's proteome to an anion exchange column, (b) eluting the anion exchange column with a high salt buffer to form an anion exchange eluate, (c) applying the anion exchange eluate to a hydrophobic interaction chromatography column, (d) eluting the hydrophobic interaction chromatography column with a low salt buffer to form a low salt eluate, (e) eluting the hydrophobic interaction chromatography column with a low salt buffer comprising an organic solvent to form a low salt plus solvent eluate, (f) fractionating the low salt eluate by isoelectric focusing and polyacrylamide electrophoresis, and (g) fractionating the low salt plus solvent eluate by isoelectric focusing and polyacrylamide electrophoresis. In some embodiments, a method of proteomic protein fractionation may further include pooling the low salt eluate and the low salt plus solvent eluate before fractionating either the low salt eluate or the low salt plus solvent eluate.

In some embodiments, a device for proteomic protein fractionation may include a first fractionator configured to receive a protein mixture, a second fractionator in fluid contact with the first fractionator, and a third fractionator in fluid contact with the first or second fractionator, wherein the first fractionator comprises an anion exchange column, the second fractionator comprises a hydrophobic interaction chromatography column, and the third protein fractionator comprises a size-fractionation matrix (e.g., polyacrylamide) and an isoelectric focusing matrix. A device may be configured and arranged to receive a protein mixture in a solution volume of less than about 1.0 mL, about 1.0 mL, or more than about 1.0 mL.

A system for proteomic protein fractionation may include (a) a first fractionator configured to receive a protein mixture, (b) a first fractionator eluate connector in fluid contact with the first fractionator and configured to collect eluate from the first fractionator, (c) a second fractionator in fluid contact with the first fractionator eluate connector, (d) a second fractionator eluate connector in fluid contact with the second fractionator and configured to collect eluate from the second fractionator, and (e) a third fractionator in fluid contact with the second fractionator eluate connector, wherein the first fractionator comprises an anion exchange column, the second fractionator comprises a hydrophobic interaction chromatography column, and the third protein fractionator comprises a size-fractionation matrix and an isoelectric focusing matrix.

A system may be configured and arranged wherein the first fractionator eluate connector is configured to meter the flow leaving the first fractionator into the second fractionator. In some embodiments, a system may further include a processor operably linked to the first fractionator eluate connector, wherein the processor conditionally regulates the metered flow (e.g., based on salt concentration of the eluate).

A system may be configured and arranged wherein the second fractionator eluate connector is configured to meter the flow leaving the second fractionator into the third fractionator. In some embodiments, a system may further include a processor operably linked to the second fractionator eluate connector, wherein the processor conditionally regulates the metered flow (e.g., based on salt concentration of the eluate).

BRIEF DESCRIPTION OF THE DRAWINGS

Some embodiments of the disclosure may be understood by referring, in part, to the following description and the accompanying drawings, wherein:

FIG. 1 shows a basic sequential prefractionation scheme using a three fraction strategy.

FIG. 2A shows a 2DE analysis of HT-29 human carcinoma cell line cytosol fractionated using traditional methods. The isoelectric focusing pH range was 3-10 and the SDS-PAGE dimension utilizes a 12% acrylamide gel.

FIG. 2B shows a 2DE analysis of HT-29 human carcinoma cell line cytosol fractionated using a method comprising an anion exchange chromatography prefractionation step (Fraction 1). The isoelectric focusing pH range was 3-10 and the SDS-PAGE dimension utilizes a 12% acrylamide gel.

FIG. 2C shows a 2DE analysis of HT-29 human carcinoma cell line cytosol fractionated using a method comprising an anion exchange chromatography prefractionation step and a hydrophobic interaction chromatography step (Fraction 2). The isoelectric focusing pH range was 3-10 and the SDS-PAGE dimension utilizes a 12% acrylamide gel.

FIG. 2D shows a 2DE analysis of HT-29 human carcinoma cell line cytosol fractionated using a method comprising an anion exchange chromatography prefractionation step and a hydrophobic interaction chromatography step with elution (Fraction 3). The isoelectric focusing pH range was 3-10 and the SDS-PAGE dimension utilizes a 12% acrylamide gel.

DETAILED DESCRIPTION OF THE PREFERRED EMBODIMENTS OF THE PRESENT DISCLOSURE

After the sequencing of the human genome, great interest has developed in trying to discern the complementary proteome of humans and other species. At the onset of this type of research the workhorse of parallel analysis of large numbers of proteins was two dimensional electrophoresis (2DE). While powerful, the method suffers from a number of shortcomings, and thus research has now focused on means of either alternative superior methods of proteomic analysis or ways of improving 2DE. These attempts have included attempts to improve 2DE analysis itself. These attempts that also included efforts to process a protein mixture prior to performing 2DE ("pre-fractionation"). In some embodiments of the disclosure, pre-fractionation may be configured to produce a small number of discrete fractions that are each independently analyzed by 2DE.

A protein fractionation method, according to some embodiments, may include prefractionating a protein mixture to form at least one eluate fraction and fractionating the at least one eluate fraction by 2DE. In some embodiments, prefractionating a protein mixture may include one or more chromatographic modes of fractionation. For each chromatographic mode (e.g., ion exchange chromatography and hydrophobic interaction chromatography) conditions may be selected so that two distinct protein populations (fractions) exist: a population that binds to the chromatographic resin being used, and a population that does not bind, with as little overlap as possible.

According to some embodiments, prefractionation may increase resolution by reducing the number of individual spots per gel (e.g., fewer spots per gel, but 2-5 more gels), and/or increasing the loading concentration of lower abundance proteins.

A comparison between a regular 2DE gel using a broad pH range strip (i.e. pH from 3-10) and narrower pH range 2DE (e.g., pH 4-7) gel may reveal that the number of spots about double on the latter gel. Without being limited to any particular mechanism of action, this may be broadly interpreted as showing on average about half of the spots on the broad range gel may include a plurality of protein species and the other about half include a single protein species.

Pre-fractionation according to some embodiments of the disclosure, may result in an increased total number of 2DE spots (fractions) compared with 2DE without prefractionation. Without being limited to any particular model or mechanism of action, this may be due, in part, to separation of the total protein into from 3-6 2DE gels rather than being run on a single gel. For example, rather than having all protein species on a single gel, they may be split (e.g., about evenly spilt) onto several gels. Where 3 prefractionation fractions are used, each fraction may contain about one third of the total number of protein species. This may yield cleaner separations with fewer multi-protein spots.

The total number of spots may also be due, in part, to enrichment (e.g., of low abundance proteins). Prefractionation fractions may contain fewer protein species than an unfractionated sample such that lower abundance proteins that would be present at an undetectable concentration in an unfractionated sample, may be detectable in the prefractionated sample. For example, if all species are run in a single sample, the loading limit of a single gel may limit the mass of protein to be loaded to about 30 to about 40 µg. On the other hand, after prefractionation, each gel to be run can be loaded with the same mass of protein (e.g., 30-40 µg). Thus, from about 3× to about 6× the mass of protein may be fractionated compared to non-prefractionated protein.

In some embodiments, there may be a trade off between spectrum of proteins visualized and resolution. For example, by running a 2DE gel over a broad pH range (e.g., 3-10), it may be possible to view the maximum number of protein species. However, the resolution (e.g., physical space) between each species may be relatively low. On the other hand, the resolution may be improved by running a 2DE over a narrower pH range (e.g., 4-7), but the number of species observed may be reduced (e.g., substantially reduced) (species with a pI over 7, if viewable at all, may cluster in a single spot).

According to a specific example embodiment of the disclosure, a fractionation method may include prefractionating a protein mixture (e.g., in two dimensions) to produce up to about 6 prefractionation fractions and running each prefractionation fraction on a 2DE gel that is optimized (or approximately optimized) for the species in each respective fraction. For example, in a 3-fraction fractionation scheme (e.g., IEC→HIC→2DE), a ion exchange bind fraction may be run on a pH 6-10 gel. In addition, the ion exchange column no-bind fraction may be applied to a hydrophobic interaction column and the hydrophobic interaction no-bind and bind fractions that result may be each run on a pH 4-7 gel.

In some embodiments, this trade off may be mitigated or eliminated with prefractionation. By contrast, non-prefractionated protein samples may have to be run on both broad and narrow pH 2DE gels to achieve the same spectrum and resolution.

The present inventor has observed that there is commonly at least one point in every elution profile where few if any proteins are eluted. In many cases, this may occur near the front of the elution scheme. The few proteins that are eluted at this stage ("low elution point") may include proteins that bind the chromatography resin weakly or not at all. It may be exceptionally rare to find conditions in which all proteins of a complex mixture bind to a given type of resin under typical biochemical conditions. Thus, in some embodiments, prefractionating a protein mixture may include one or more binary chromatographic modes of fractionation in which proteins are separated into binding and non-binding fractions. For example, a protein fractionation method may include prefractionating a protein mixture using two binary chromatographic modes. A first fraction may be a no-bind mode 1, a second fraction may be a bind mode 1. If each of these is applied to a second chromatographic mode, the following fractions may result:

| | | |
|---|---|---|
| 1. No-Bind Mode 1 | { | 3. No-Bind Mode 1, No-Bind Mode 2 |
| | | 4. No-Bind Mode 1, Bind Mode 2 |
| 2. Bind Mode 1 | { | 5. Bind Mode 1, No-Bind Mode 2 |
| | | 6. Bind Mode 1, Bind Mode 2 |

By using the low elution point, a protein fractionation method may, according to some embodiments of the disclosure, achieve as clean a separation as is theoretically possible under a given set of starting conditions.

By contrast, a protein fractionation method that includes only a single chromatographic mode of prefractionation, may separate proteins less efficiently and result in fractions with multiple protein species (PPF) and/or proteins that are present in multiple fractions (FPP). Without being limited to any particularly mechanism of action, this may be due to the fact single chromatographic modes rarely, if ever, have multiple low elution points.

Protein fractionation methods that use low elution point prefractionation, in some embodiments, may be executed more quickly since it may be less encumbered by the need to collect multiple fractions. A method may also be performed quickly by choosing the elution composition for the first chromatographic mode so that the eluate is in condition for direct application to the second chromatographic mode (e.g., no desalting required). Resolving power of a fractionation method may be time dependent. In other words, with an unlimited amount of time and the right conditions (e.g., a shallow elution gradient), almost any two protein species may be separated into distinct fractions. A fractionation method, according to some embodiments of the disclosure, may avoid the use of elution gradients and the associated time required to execute them, yet retain substantial resolving power using low elution point prefractionation. Indeed, in some embodiments, prefractionating a protein mixture in 2 dimensions (e.g., anion exchange chromatography and hydrophobic interaction chromatography) may be completed in about 30 minutes or less.

Fractionation methods that generate a large number of fractions after prefractionation (e.g., gradient methods) greatly increase the number of 2DE gels that must be run. The binary nature of prefractionation and the small number of resulting fractions (e.g., 6 or less), according to some embodiments of the disclosure, may permit additional time savings to be realized during 2DE fractionation since few 2DE gels must be run. This time savings may be particularly acute where the repeatability of 2DE is low, requiring each gel to be run in duplicate, triplicate, or more.

A binary chromatographic mode, in some embodiments, may be performed without resort to an elution gradient. For example, prefractionating a protein mixture before 2DE may include eluting an anion exchange column and/or a hydrophobic interaction column with composition having fixed concentration(s) of its component(s). Thus, unlike embodiments in which the concentration of one or more components may vary (e.g., increasing or decreasing salt concentration), the composition may remain unchanged or substantially unchanged throughout the time that it is applied to the pre-fractionation column.

The present disclosure provides devices, systems, and methods for proteomic fractionation that may increase the number of protein spots visualized by 2DE analysis, and may allow enrichment of proteins normally not detectable by standard 2DE analysis. Devices, systems, and methods are provided for separation of a mixture of proteins into several discrete fractions having specific physiochemical properties. Fractions may be further analyzed by one or more additional discriminating techniques including, without limitation, two dimensional electrophoresis (2DE) or high resolution chromatography.

A mixture of proteins, according to some embodiments, includes at least two proteins with differing structures (e.g., primary, secondary, tertiary, or quaternary). In some embodiments, a mixture of proteins may contain substantially all proteins in the proteome of an organism, a tissue and/or cell type.

A protein mixture may be prepared by standard techniques including removal of insoluble materials. Additionally, protein concentration may be determined for the mixture, e.g., when quantitative comparisons of individual proteins between two or more experimental treatments are involved. When there are multiple experimental treatments involved each treatment may be processed separately.

In some embodiments, a protein mixture may be sequentially subjected to two chromatographic techniques. First a known quantity of a protein mixture may be applied to an anion exchange column. This column may be selected to bind all proteins with a significant negative surface charge at the pH of the buffer chosen. Proteins that do not bind to the anion exchange column may be collected as fraction 1 and may be characterized as "high pI fraction".

Bound proteins may be eluted from the anion exchange column using a high salt buffer (e.g., about 0.5 M or higher). Eluted proteins may be applied (e.g., directly) to second column including, without limitation, a hydrophobic interaction column. According to some embodiments of the disclosure, a hydrophobic interaction column may utilize a C4 (t-butyl) functional group immobilized on a hydrophobic support (as opposed C4 functional moiety attached to a silica or related supports typically used in reversed phase chromatography).

Hydrophobic interaction chromatography may be conducted in a high salt buffer (e.g., about 0.5 M or higher) producing an environment in which moderately to weakly hydrophobic proteins will bind to the chromatography resin. (In reversed phase chromatography, only proteins with moderate to high hydrophobicity will bind.) Again proteins that do not interact with the column are collected and this fraction is defined as low pI hydrophilic fraction (fraction 2).

One of ordinary skill in the art will recognize that the exact concentration of salt solution used to elute an ion exchange column or a hydrophobic interaction column will influence the nature of the proteins eluted. Thus, in some embodiments of the disclosure, a loading and/or elution buffer may have a high salt concentration. For example, a high salt buffer may have a salt concentration of about or over 500 mM, about or over 1.0 M, and/or about or over 1.7 M. In other embodiments, a loading or elution buffer may have a low salt concentration. For example, a low salt buffer may have a salt concentration of about or under 500 mM, about or under 100 mM, about or under 50 mM, and/or about or under 25 mM. In some embodiments, a salt gradient may be used to elute a column.

In some embodiments, bound proteins may be eluted from this column either with two sequential elution washes including a first a low salt buffer (e.g., about or less than 0.1 M), followed by the same low salt buffer also containing an organic solvent such as methanol (e.g., 30% v/v methanol). In other embodiments, bound proteins may be eluted in a single wash using a low salt buffer containing an organic solvent. (This elution scheme is actually a combination of hydrophobic interaction chromatography which typically uses low salt for elution and reversed phase chromatography which typically uses an organic solvent for elution.) If a single fraction elution scheme is used the fraction is considered the low pI, hydrophobic fraction. If a two step elution scheme is used the first elution fraction is considered the mildly hydrophobic low pI fraction, and the second fractions is considered the strongly hydrophobic low pI fraction.

Typically, each of the fractions may be concentrated using standard practices. In some embodiments, all fractions except fraction 1 may be desalted, again by standard practices, to remove the high salt and organic solvents which may interfere with later high resolution analysis. Total protein may be determined for each fraction. For two dimensional electrophoresis, an appropriate quantity of each fraction is diluted in standard denaturing buffer and loaded onto IPG isoelectric focusing strips for analysis. For high resolution chromatography, an appropriate quantity is loaded into a sample loop without modification. FIG. 2 shows 2DE analysis of the HT-29 human colon carcinoma cell line with standard 2DE and with the 3 fraction-prefractionation scheme described above.

A fraction may include an aliquot of the eluate from a column (e.g., taken as a discrete time or elution condition), a band from a 1-dimensional gel, or a spot from a 2-dimensional gel.

In some embodiments of the disclosure, a fractionation method may produce one or more fractions (e.g., 2DE spots) that contain a single protein species (PPF). For example, from about 10% to about 20%, from about 20% to about 30%, from about 30% to about 40%, from about 40% to about 50%, or more than about 50% of the fractions produced by a fractionation method may contain a single protein species. The foregoing percentages may be calculated as a function of the total number of fractions (e.g., spots) on a specific 2DE gel and/or the total number of fractions (e.g., spots) derived from an original protein sample. In the latter case, the total number of 2DE fractions may include fractions from more than one 2DE gel, for example, where more than one fraction from the prefractionation is subjected to 2DE fractionation.

In some embodiments of the disclosure, a fractionation method may produce one or more fractions (e.g., 2DE spots) that contain about 3 protein species (PPF) or less. For example, from about 50% to about 60%, from about 60% to about 70%, from about 70% to about 80%, from about 80% to about 90%, or more than about 90% of the fractions produced by a fractionation method may contain about 3 protein species or less. The foregoing percentages may be calculated as a function of the total number of fractions (e.g., spots) on a specific 2DE gel and/or the total number of fractions (e.g., spots) derived from an original protein sample. In the latter case, the total number of 2DE fractions may include fractions from more than one 2DE gel, for example, where more than one fraction from the prefractionation is subjected to 2DE fractionation.

A fractionation method, according to some embodiments of the disclosure, may separate one or more proteins into distinct fractions (e.g., 2DE spots) (FPP). For example, from about 10% to about 20%, from about 20% to about 30%, from about 30% to about 40%, from about 40% to about 50%, or more than about 50% of the proteins are contained in individual fractions. The foregoing percentages may be calculated as a function of the number of proteins in a particular fraction derived from a prefractionation step and/or the total number of proteins in the original protein sample.

A mixture or proteins prefractionated according to some embodiments of the disclosure (e.g., using two axes of separation) may generate more spots on a 2DE gel than a mixture of proteins that is not prefractionated. For example, a prefractionated protein mixture may generate more than about 2 times, more than about 4 times, more than about 6 times, more than about 8 times, more than about 10 times, or more than about 20 times the number of 2DE spots as a protein mixture that is not prefractionated run under the same 2DE conditions.

Accordingly, a two-axis prefractionation may increase (e.g., greatly increase) the global resolving power of a fractionation method.

A device and/or system of the disclosure may include a first, second and third protein fractionator. A first protein fractionator may include an ion exchange column and one or more connectors. A second protein fractionator may include a hydrophobic interaction column and one or more connectors. A third protein fractionator may include a size-fractionation matrix, an isoelectric focusing matrix, and/or combinations thereof. A third protein fractionator may further include one or more connectors. Connectors may link one fractionator to another such that eluate from one fractionator is intermittently, continuously, or conditionally fed into another fractionator. For example, a device may include an anion exchange column connected to a hydrophobic interaction column, which is in turn connected to a 2DE gel and the connections allow passage of eluate only when a desired solvent and/or salt concentration (or range) is present in the eluate. A system of the disclosure may include one or more dispensers that meter the size of fractions collected from a fractionator and/or the amount, kind, and/or concentration of buffer applied to a fractionator. A system of the disclosure may include a power source, potentiostat (e.g., to control current to the 2DE gel), a processing device (e.g., a processor), and/or a display. Systems and devices of the disclosure may be configured to handle sample volumes of more than one milliliter or may be miniaturized to handle smaller sample volumes (e.g., microliters, nanoliters, or less).

Example 1

Four T-75 flasks of HT-29 carcinoma cell cultures were grown until confluent in McCoy's modified medium (Gibco) with 10% FBS, and 1% Penicillin-Streptomycin (Gibco). Media was removed and cultures were rinsed two times with PBS, then lysed with a low ionic strength lysis buffer ((50 mM Tris, pH 7.5, 10 mM DTT, and a protease Inhibitor cocktail (Sigma diluted 100:1), followed by 3 rapid freeze/thaw cycles. Individual lyses were pooled and centrifuged for 20 minutes at 24,000×G at four degrees Celsius, followed by filtering with a 0.2 µm syringe filter. Total protein was determined by Bradford's dye binding assay. An aliquot was diluted 5:1 in 2DE lysis buffer (7 M urea, 2 M thiourea, 4% CHAPS, 4 mM tributyl phosphine (TBP), 0.5% ampholyte solution, and a trace of bromophenol blue) and analyzed by 2DE and is designated the traditional method.

Three milligrams of the cytosolic extract was applied to an ion exchange column (Poly-Prep gravity column (Biorad) containing 1 ml bed volume of MacroPrep Q ion exchange media (Biorad)) pre-equilibrated with 5 bed volumes of 50 mM Tris, pH 7.5. The flow-through was collected as fraction 1. After a 4 bed volume wash with 50 mM Tris, pH 7.5, the bound protein was eluted with 1.7 M ammonium sulfate in 25 mM Tris pH 7.5.

The elutate was then directly applied to a hydrophobic interaction chromatography column (Poly-prep column (Biorad) containing 1 ml bed volume of Macro-Prep HIC media (Biorad)) pre-equilibrated with 5 volumes of 1.7 M ammonium sulfate in 25 mM Tris pH 7.5. The flow-through was collected as fraction 2. After a 4 volume wash with 1.7 M ammonium sulfate in 25 mM Tris pH 7.5, the bound protein was eluted with 25 mM Tris, pH 7.5 containing 30% methanol, as fraction 3. All three fractions were concentrated using Ultra 4 centrifugal concentrators (Millipore), and fractions 2 and 3 were also desalted using the same concentrators but re-diluting the concentrate with 25 mM Tris, pH 7.5 twice. Total protein was determined for all fractions.

Each fraction was diluted 5:1 in 2DE lysis solution. For 2DE, 40 µg of protein was loaded overnight onto 11 cm immobilized pH gradient (IPG) strips (pH range 3-10) by the passive rehydration method. Isoelectric focusing (IEF) was conducted using a Multiphor II (GE Healthcare). After IEF, IPG strips were equilibrated for 20 minute in an equilibrium buffer (6 M urea, 50 mM Tris pH 6.8, 2% w/v SDS, 30% glycerol, and a trace of bromophenol blue). The second dimension (SDS PAGE) was conducted on a Hoeffer 600 (GE Healthcare) vertical electrophoresis unit using 12% total acrylamide homogeneous gels. After electrophoresis, gels were silver stained by the method of Blum. Stained gels were scanned on an HP psc 750 printer/scanner/copier. Results are shown in FIGS. 2A-D.

As will be understood by those skilled in the art, other equivalent or alternative devices, systems, and/or methods for fractionating proteomic proteins and/or polypeptides can be envisioned without departing from the essential characteristics thereof. For example, devices of the disclosure may be manufactured in either a handheld or a tabletop configuration, and may be operated intermittently or continuously. Moreover, individuals skilled in the art would recognize that additional chromatographic techniques or separation methods may be incorporated, e.g., to partially or completely remove lipids, carbohydrates, and/or nucleic acids. Also, the temperature, pressure, and acceleration (e.g., spin columns) at which each step is performed may be varied. Additionally, detectors may be configured and positioned to detect the conditions, progress, and/or results of fractionation. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

What is claimed is:

1. A method of proteomic protein fractionation comprising:
   a) applying a protein mixture to an anion exchange column;
   b) collecting a first fraction comprising the nonbinding protein flowthrough that passes through the anion exchange column;
   c) eluting the anion exchange column with a high salt buffer to form an anion exchange eluate wherein the high salt buffer comprises 0.5 M salt or greater;
   d) applying the anion exchange eluate to a hydrophobic interaction chromatography column;
   e) collecting a second fraction comprising the nonbinding protein flowthrough that passes through the hydrophobic interaction chromatography column;
   f) eluting the hydrophobic interaction chromatography column with a low salt buffer, wherein the low salt buffer comprises 0.1 M salt or less, to form a low salt eluate;
   g) collecting a third fraction comprising the low salt eluate eluted from the hydrophobic interaction chromatography column;
   h) fractionating the first fraction by two-dimensional electrophoresis comprising isoelectric focusing and sodium dodecyl sulfate polyacrylamide electrophoresis on a first gel;
   i) fractionating the second fraction by two-dimensional electrophoresis comprising isoelectric focusing and sodium dodecyl sulfate polyacrylamide electrophoresis on a second gel; and
   j) fractionating the third fraction by two-dimensional electrophoresis comprising isoelectric focusing and sodium dodecyl sulfate polyacrylamide electrophoresis on a third gel,
   thereby generating more than 2 times the number of protein spots on the combination of the first gel, the second gel and the third gel, as compared to the number of spots on a single gel from a sample of the protein mixture that is not prefractionated by the anion exchange column and/or the hydrophobic interaction chromatography column, but is fractionated by two-dimensional electrophoresis comprising isoelectric focusing and polyacrylamide electrophoresis.

2. A method according to claim 1 further comprising eluting the hydrophobic interaction chromatography column with a low salt buffer comprising an organic solvent to form a fourth fraction comprising a low salt plus solvent eluate, and fractionating the fourth fraction by isoelectric focusing and polyacrylamide electrophoresis.

3. A method according to claim 1, wherein the hydrophobic interaction chromatography column comprises a C4 (t-butyl) functional group immobilized on a hydrophobic support.

4. A method according to claim 1, wherein the isoelectric focusing pH range is from about 3 to about 10.

5. A method according to claim 1, wherein the polyacrylamide electrophoresis is performed on a gel comprising from about 10% to about 12% by weight polyacrylamide.

6. A method according to claim 1, wherein the low salt buffer comprising an organic solvent comprises 0.1 M salt or less.

7. A method according to claim 1, wherein the protein mixture comprises substantially every protein in an organism's proteome.

8. A method according to claim 7, wherein the organism is selected from the group consisting of microbes, invertebrates, and vertebrates.

9. A method according to claim 8, wherein the vertebrate is selected from the group consisting of humans and non-human mammals.

10. A method according to claim 1, wherein the eluting the anion exchange column with a high salt buffer to form an anion exchange eluate comprises maintaining the components of the high salt buffer at a constant concentration throughout the eluting.

11. A method according to claim 1, wherein the eluting the hydrophobic interaction chromatography column with a low salt buffer to form a low salt eluate maintaining the components of the low salt buffer at a constant concentration throughout the eluting.

12. A method according to claim 1, further comprising:
   fractionating the first fraction by two-dimensional electrophoresis comprising isoelectric focusing at a pH range of from about 7 to about 10 and polyacrylamide electrophoresis on the first gel.

13. A method according to claim 1, further comprising:
   fractionating the second fraction by two-dimensional electrophoresis comprising isoelectric focusing at a pH range of from about 4 to about 7 and polyacrylamide electrophoresis on the second gel.

14. A method according to claim 1, further comprising:
   fractionating the third fraction by two-dimensional electrophoresis comprising isoelectric focusing at a pH range of from about 4 to about 7 and polyacrylamide electrophoresis on the third gel.

15. A method of proteomic protein fractionation comprising:
   a) applying a protein mixture comprising up to every protein in an organism's proteome to an anion exchange column;
   b) collecting a first fraction comprising the nonbinding protein flowthrough that passes through the anion exchange column;

c) eluting the anion exchange column with a high salt buffer, wherein the high salt buffer comprises 0.5 M salt or greater without a gradient, to form an anion exchange eluate;
d) applying the anion exchange eluate to a hydrophobic interaction chromatography column;
e) collecting a second fraction comprising the nonbinding protein flowthrough that passes through the hydrophobic interaction chromatography column;
f) eluting the hydrophobic interaction chromatography column with a low salt buffer, wherein the low salt buffer comprises 0.1 M salt or less without a gradient, to form a low salt eluate;
g) collecting a third fraction comprising the low salt eluate eluted from the hydrophobic interaction chromatography column;
h) optionally eluting the hydrophobic interaction chromatography column with a low salt buffer comprising an organic solvent to form a fourth fraction comprising a low salt plus solvent eluate;
i) fractionating the first fraction by two-dimensional electrophoresis comprising isoelectric focusing and sodium dodecyl sulfate polyacrylamide electrophoresis on a first gel;
j) fractionating the second fraction by isoelectric focusing and sodium dodecyl sulfate polyacrylamide electrophoresis on a second gel;
k) fractionating the third fraction comprising the low salt eluate by isoelectric focusing and sodium dodecyl sulfate polyacrylamide electrophoresis on a third gel, and
l) optionally fractionating the fourth fraction comprising the low salt plus solvent eluate by isoelectric focusing and polyacrylamide electrophoresis on a fourth gel;

thereby generating more than 2 times the number of protein spots on the combination of the first, second and third gels, or the combination of the first, second, third and fourth gels, as compared to the number of spots on a single gel from a sample of the protein mixture that is not prefractionated by the anion exchange column and/or the hydrophobic interaction chromatography column, but is fractionated on a single gel by two-dimensional electrophoresis comprising isoelectric focusing and polyacrylamide electrophoresis.

16. The method according to claim 15, further comprising pooling the low salt eluate and the low salt plus solvent eluate to form a fifth fraction and fractionating the fifth fraction by two-dimensional electrophoresis comprising isoelectric focusing and sodium deodecyl sulfate polyacrylamide electrophoresis on a fifth gel.

17. A method according to claim 15, further comprising:
fractionating the first fraction by two-dimensional electrophoresis comprising isoelectric focusing at a pH range of from about 7 to about 10 and polyacrylamide electrophoresis on a first two-dimensional electrophoresis gel.

18. A method according to claim 15, further comprising:
fractionating the second fraction by two-dimensional electrophoresis comprising isoelectric focusing at a pH range of from about 4 to about 7 and polyacrylamide electrophoresis on a second two-dimensional electrophoresis gel.

19. A method according to claim 15, further comprising:
fractionating the fourth fraction by two-dimensional electrophoresis comprising isoelectric focusing at a pH range of from about 4 to about 7 and polyacrylamide electrophoresis on the third gel.

* * * * *